United States Patent
Shen et al.

(10) Patent No.: US 10,316,033 B2
(45) Date of Patent: Jun. 11, 2019

(54) PROCESS OF SYNTHESIZING SUBSTITUTED PYRIDINE AND PYRIMIDINE COMPOUND

(71) Applicants: SHANGHAI INSTITUTE OF MATERIA MEDICA, CHINESE ACADEMY OF SCIENCES, Shanghai (CN); SHANDONG LUOXIN PHARMACEUTICAL GROUP STOCK CO., LTD., Linyi, Shandong (CN)

(72) Inventors: Jingkang Shen, Shanghai (CN); Tao Meng, Shanghai (CN); Ting Yu, Shanghai (CN); Lanping Ma, Shanghai (CN); Xin Wang, Shanghai (CN); Lin Chen, Shanghai (CN)

(73) Assignees: Shanghai Institute of Materia Medica, Chinese Academy of Sciences, Shanghai (CN); Shandong Luoxin Pharmaceutical Group Stock Co., Ltd., Shandong (CN)

( * ) Notice: Subject to any disclaimer, the term of this patent is extended or adjusted under 35 U.S.C. 154(b) by 0 days.

(21) Appl. No.: 15/561,003

(22) PCT Filed: Mar. 24, 2016

(86) PCT No.: PCT/CN2016/077259
§ 371 (c)(1),
(2) Date: Sep. 22, 2017

(87) PCT Pub. No.: WO2016/150396
PCT Pub. Date: Sep. 29, 2016

(65) Prior Publication Data
US 2018/0079749 A1    Mar. 22, 2018

(30) Foreign Application Priority Data
Mar. 25, 2015 (CN) .......................... 2015 1 0134261

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS

2008/0081809 A1* 4/2008 Duggan ............... C07D 471/04
                                                    514/232.5
2008/0194546 A1* 8/2008 Hummersone ...... C07D 475/06
                                                    514/221

FOREIGN PATENT DOCUMENTS

| CN | 102887895 A | 1/2013 |
|---|---|---|
| CN | 103588792 A | 2/2014 |
| WO | WO 2008/023161 A1 | 2/2008 |
| WO | WO 2013/016999 A1 | 2/2013 |

OTHER PUBLICATIONS

PCT International Search Report dated Jul. 6, 2016 issued in PCT/CN2016/077259 (WO2016150396) (with translation).
European Extended Search Report dated Jul. 19, 2018 issued in EP 16767773.1.
European Communication pursuant to Rules 70(2) and 70a(2) EPC dated Aug. 7, 2018 issued in EP 16767773.1.
Pike et al. (2013) "Optimization of potent and selective dual mTORC1 and mTORC2 inhibitors: The discovery of AZD8055 and AZD2014", *Bioorganic & Medicinal Chemistry Letters*, Pergamon, Amsterdam, NL, 23(5): 1212-1216.

* cited by examiner

*Primary Examiner* — Bruck Kifle
(74) *Attorney, Agent, or Firm* — Tom Hunter; Weaver Austin Villenueve & Sampson LLP

(57) ABSTRACT

Provided is a process of synthesizing a substituted pyridine and pyrimidine compound. Particularly, provided is a method for preparing a compound of formula III via a compound of formula II', wherein the definition of each of groups is as described as the description. Compound with other methods, the method in the present invention has features of high yield and a result product being easier to separate.

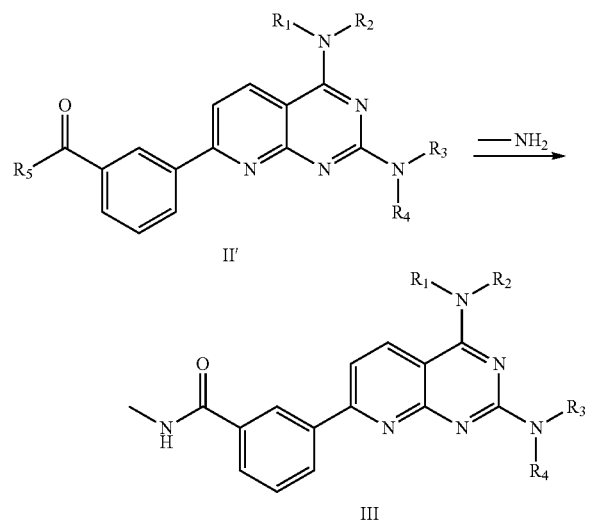

14 Claims, No Drawings

PROCESS OF SYNTHESIZING SUBSTITUTED PYRIDINE AND PYRIMIDINE COMPOUND

CROSS-REFERENCE TO RELATED APPLICATIONS

This application is a U.S. 371 National Phase of PCT/CN2016/077259, filed on Mar 24, 2016, which claims priority to Chinese Patent Application No: 201510134261.7, filed on Mar 25, 2015, both of which are incorporated herein by reference in their entirety for all purposes.

FIELD OF THE INVENTION

The invention relates to the field of drug synthesis, particularly, the present invention provides a process of synthesizing a substituted pyridine and pyrimidine compound.

BACKGROUND OF THE INVENTION

Mammalian target of rapamycin (mTOR) is an important signaling transduction molecule that regulates cell growth and proliferation, and is also a protein kinase. It plays an important role mainly by activating ribosomal 40s subunit S6K protein kinase and inhibiting eukaryotic initiation factor 4E (eIF-4E) binding protein 1. The pathway integrates signals from nutrients, energy, and growth factors to regulate a large number of vital process. The abnormal activation of mTOR signaling pathway relates to the occurrence, development and metastasis of tumor.

Rapamycin and its derivatives are mTOR signaling specific inhibitors. At present, the first generation mTOR allosteric inhibitor such as Rapamycin Temsirolimus/Torisel, and Everolimus/Afinitor has been used for the treatment of immune, cardiovascular, malignant tumor and other critical diseases, The mTOR related clinical trials have accumulated to more than 1600 items (clinicaltrials.gov), reflecting a high attention on mTOR pathway in the medicine circles and the drug development circles. However, recent studies have found that human mTOR has at least two functional protein complexes, mTORC1 and mTORC2, which mediate both related and independent physiological and pathological mechanisms. Studies have shown that rapamycin, as an allosteric inhibitor, do not directly target mTORC2, and do not completely block mTORC1 either, therefore, the full therapeutic potential of rapamycin as mTOR targeting drugs cannot be realized.

Substituted pyridine and pyrimidine compounds (Compound A and Compound B) shown in formula A and formula B, as a ATP-competitive selective inhibitor of mTOR shows very good antitumor activity in vivo, good pharmacokinetic properties and good safety, the results of pharmacodynamic study are shown in Chinese patent (201310068888.8), PCT international patent application (PCT/CN2014/072678), and Bioorganic & Medicinal Chemistry Letters 23 (2013) 1212-1216.

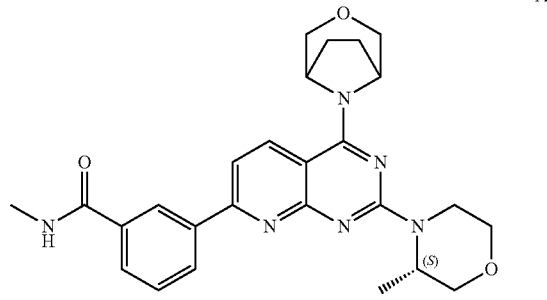

A

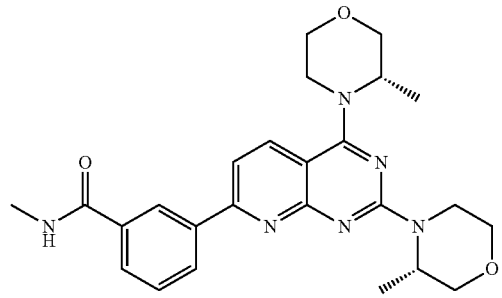

B

However, the methods for preparation the A compound and B compound described in the prior art have many problems, such as low yield, various impurities and unsuitable for industrial production. In summary, a synthetic process of low cost, high purity and suitable for industrial production of substituted pyridine and pyrimidine compound is urgently needed in this field.

SUMMARY OF THE INVENTION

The objective of the present invention is to provide a synthetic process of low cost, high purity and suitable for industrial production of substituted pyridine and pyrimidine compound.

In the first aspect of the invention, a method for preparing compound of formula III is provided.

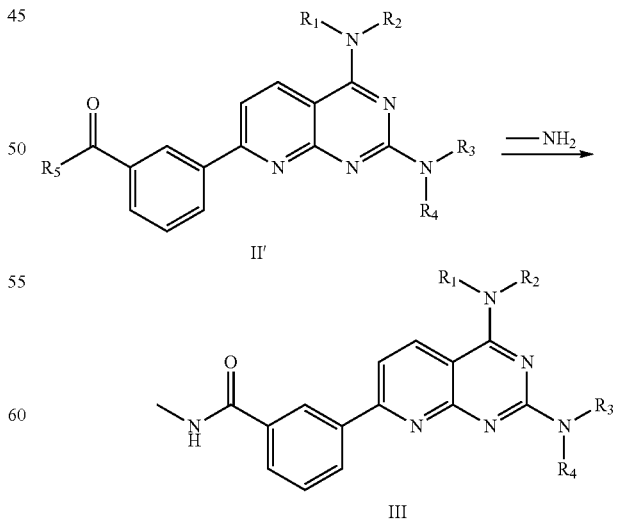

(7) reacting a compound of formula II' with methylamine or the salt thereof to provide a compound of formula III;

wherein $R_1$, $R_2$, $R_3$ and $R_4$ are each independently selected from the group consisting of substituted or unsubstituted C1-C4 alkyl, substituted or unsubstituted $C_1$-$C_4$ ester group;

or $R_1$, $R_2$ and the adjacent —N— together form a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

or $R_3$, $R_4$ and the adjacent —N— together constitute a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring.

$R_5$ is selected from the group consisting of $C_1$-$C_4$ alkoxy (preferably methoxyl or ethoxy), chlorine atom, bromine atom, hydroxyl, or active ester group

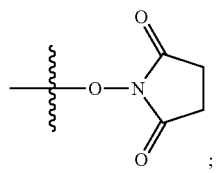

The substitution is that one or more hydrogen atoms on a group are replaced by substituents selected from the group consisting of halogens, $C_1$-$C_4$ alkyl.

The methylamine or the salt thereof is selected from the group consisting of methylamine methanol solution, methylamine ethanol solution, methylamine aqueous solution, methylamine tetrahydrofuran solution, methylamine hydrochloride, or methylamine sulfate, etc.

In another preferred embodiment, in the step (7), when $R_5$ is chlorine atom, bromine atom or active ester group

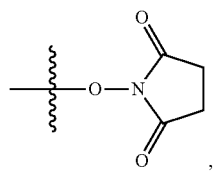

the said reaction is carried out in the presence of a base; preferably, the base is selected from the group consisting of diisopropylethylamine, triethylamine, pyridine; preferably triethylamine or diisopropylethylamine.

In another preferred embodiment, in the step (7), when $R_5$ is hydroxy, the reaction is carried out in the presence of a base; preferably, the base is selected from the group consisting of diisopropylethylamine, triethylamine, 4-dimethylaminopyridine, preferably diisopropylethylamine.

In another preferred embodiment, in the step (7), when $R_5$ is hydroxy, the reaction is carried out in the presence of a condensation reagent and/or an activator; more preferably, the condensation reagent is selected from the group consisting of EDCI, DIC, DCC, PyBOP or HATU, preferably EDCI; and/or the activator is selected from the group consisting of HOBT, DMAP, 4-PPY, HOAT or NHPI, preferably HOBT.

In another preferred embodiment, in the step (7), when $R_5$ is hydroxyl, the reaction temperature is 20-60° C.

In another preferred embodiment, in the step (7), when $R_5$ is hydroxyl, the methylamine or the salt thereof is selected from the group consisting of methylamine aqueous solution, methylamine tetrahydrofuran solution, or methylamine hydrochloride.

In another preferred embodiment, in the step (7), the reaction is carried out in an inert solvent, and preferably the inert solvent is selected from the group consisting of benzene, xylene, toluene, dichloromethane, chloroform, tetrahydrofuran, 1,4-dioxane, N,N-dimethylformamide, N,N-diethylformamide, N, N-dimethylacetamide, acetonitrile, or the combinations thereof, more preferably acetonitrile, dichloromethane or N, N-dimethylformamide.

In another preferred embodiment, in the step (7), when $R_5$ is $C_1$-$C_4$ alkoxy, the reaction is carried out with or without the presence of a base; preferably, the base is selected from the group consisting of potassium carbonate, sodium carbonate, sodium bicarbonate, or the combinations thereof; preferably potassium carbonate.

In another preferred embodiment, in the step (7), when $R_5$ is $C_1$-$C_4$ alkoxy, the reaction temperature is 20-90° C.

In another preferred embodiment, in the step (7), when $R_5$ is $C_1$-$C_4$ alkoxy, the reaction time is 12-48 h.

In another preferred embodiment, in the step (7), when $R_5$ is $C_1$-$C_4$ alkoxy group, the reaction can also be carried out in a solvent selected from the group consisting of methylamine methanol solution, methylamine ethanol solution, methylamine aqueous solution, or the combinations thereof.

In another preferred embodiment, in the step (7), when $R_5$ is $C_1$-$C_4$ alkoxy, the mass ratio of the compound of formula II' to methylamine is 1/10~1/500.

In another preferred example, the method also optionally comprises the step:

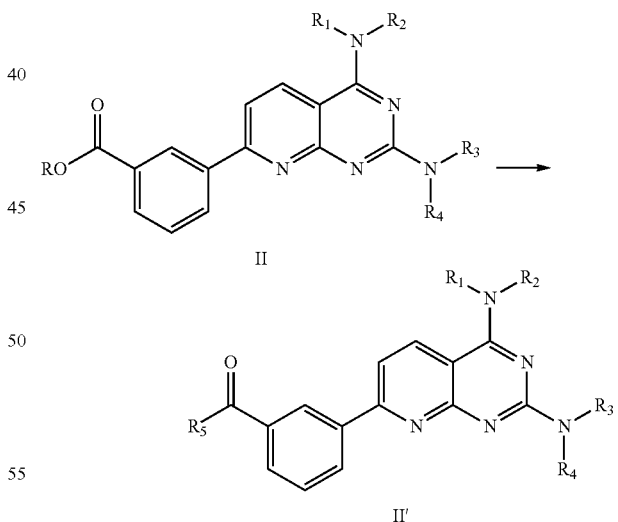

reacting the compound of formula II to provide the compound of formula II':

wherein, R is selected from the group consisting of $C_1$-$C_4$ alkyl, preferably methyl or ethyl; and the other groups are defined as above;

and RO— and $R_5$— are different groups.

In another preferred embodiment, when $R_5$ is hydroxyl, the reaction is a hydrolysis reaction, and the hydrolysis reaction is carried out under the catalysis of an alkaline catalyst selected from the group consisting of sodium hydroxide, lithium hydroxide, potassium hydroxide, or the combinations thereof.

In another preferred embodiment, the reaction temperature in the hydrolysis reaction is 20-80° C.

In another preferred example, the reaction time in the hydrolysis reaction is 0.5-12 h.

In another preferred case, the solvent in the hydrolysis reaction is methanol, ethanol, water, tetrahydrofuran, or the combinations thereof.

In another preferred case, when $R_5$ is a chlorine atom or a bromine atom, the reaction is carrying out hydrolysis reaction and then forming acyl chloride or acyl bromide with an acylation reagent.

In another preferred embodiment, the acylation reagent is selected from the group consisting of oxalyl chloride, thionyl chloride, phosphorus oxychloride, phosphorus trichloride, phosphorus pentachloride, phosphorus tribromide, phosphorus pentabromide, pivaloyl chloride, oxalyl bromide, or combinations thereof; preferably oxalyl chloride.

In another preferred embodiment, the acylation reaction can be carried out with or without the presence of a reaction solvent, the reaction solvent has no special restriction, as long as it does not interfere with the reaction, and, for example, is selected from one or more of dichloromethane, dimethyl sulfoxide, tetrahydrofuran, benzene, toluene, chloroform, xylene, N, N-methyl formamide, N, N-dimethyl acetamide.

In another preferred case, when $R_5$ is the active ester group

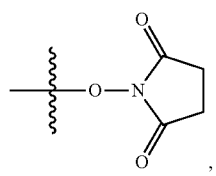 [SMILES: *ON1C(=O)CCC1=O]

the reaction is carrying out hydrolysis reaction and then forming active ester with the condensation reagent; preferably, the active ester is prepared in the presence of a condensation reagent and/or an activator; more preferably, the condensation agent is selected from the group consisting of EDCI, DIC, DCC, PyBOP or HATU, preferably EDCI; and/or the activator is selected from the group consisting of HOBT, DMAP, 4-PPY, HOAT or NHPI, preferably HOBT.

In another preferred embodiment, the compound of formula II is prepared by the following step (6):

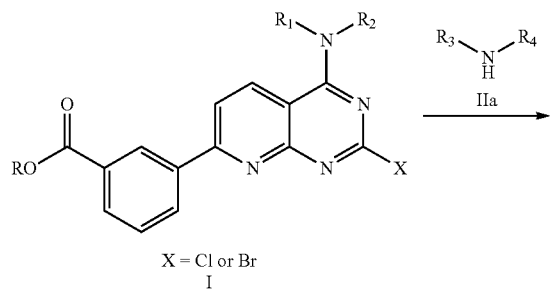

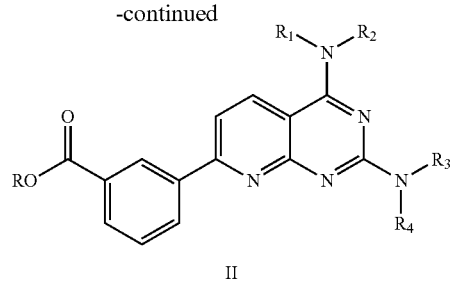

(6) reacting a compound of formula I with a compound of formula IIa or the salt thereof in the inert solvent to provide the compound of formula II.

wherein, X is selected from Cl or Br;

$R_1$, $R_2$, $R_3$, and $R_4$ are each independently selected from the group consisting of substituted or unsubstituted $C_1$-$C_4$ alkyl, substituted or unsubstituted $C_1$-$C_4$ ester group;

or $R_1$, $R_2$ and adjacent —N— together form a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring.

or $R_3$, $R_4$ and adjacent —N— together constitute a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring.

The substitution is that one or more hydrogen atoms on a group are replaced by substituents selected from the group consisting of halogen and $C_1$-$C_4$ alkyl.

In another preferred embodiment, in the step (6), the reaction is carried out in the presence of a base catalyst; preferably, the base catalyst is selected from organic bases, most preferably, the organic base catalyst is selected from the group consisting of diisopropylethylamine, N,N-dimethylaniline, or the combinations thereof, preferably diisopropylethylamine.

In another preferred embodiment, in the step (6), the reaction temperature is 80-180° C.

In another preferred embodiment, in the step (6), the reaction temperature is 12-40 h.

In another preferred embodiment, in the step (6), the solvent in the reaction is selected from the groups consisting of NMP, acetonitrile, toluene, 1,4-dioxane, DMF, xylene, or the combinations thereof.

In another preferred embodiment, in the step (6), the molar ratio of the compound of formula I to the compound of formula IIa is 1/1~1/1.5.

In another preferred embodiment, in the step (6), the compound of formula IIa is selected from the group consisting of 3-(S)-3-methyl morpholine.

In another preferred embodiment, the salt of the compound of formula IIa is hydrochloride.

In another preferred embodiment, in the method, the compound of formula I is prepared by the step (5):

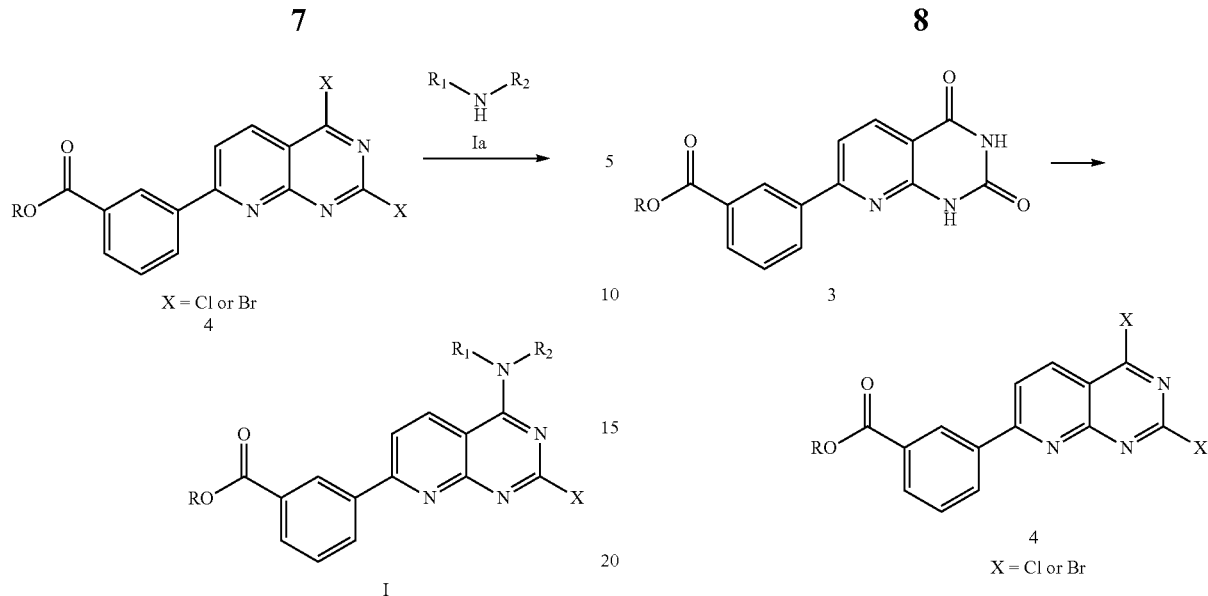

(5) reacting a compound of formula 4 with a compound of formula Ia or the salt thereof in the inert solvent to provide the compound of formula I.

wherein, X is selected from Cl or Br;

$R_1$, $R_2$ are each independently selected from the group consisting of substituted or unsubstituted $C_1$-$C_4$ alkyl, substituted or unsubstituted $C_1$-$C_4$ ester group; or $R_1$, $R_2$ and adjacent —N— together form a substituted or unsubstituted 3-10 membered heterocycle, and the heterocycle may contain 1-3 heteroatoms selected from the group consisting of N, O or S;

The substituted means that one or more hydrogen atoms on a group are replaced by substituents selected from the group consisting of halogen, and $C_1$-$C_4$ alkyl.

In another preferred embodiment, the 3-10 membered heterocycle is monocycle, bicycle, spirocycle or bridged ring.

In another preferred embodiment, the salt of the compound of the formula Ia is hydrochloride.

In another preferred embodiment, in the step (5), the reaction is carried out in the presence of a base catalyst; preferably, the base catalyst is selected from organic bases; most preferably, the organic base catalyst is selected from the group consisting of diisopropylethylamine, N,N-dimethylaniline, or the combinations thereof, preferably diisopropylethylamine.

In another preferred embodiment, in the step (5), the reaction temperature is 0-80° C., preferably 10-50° C.

In another preferred embodiment, in the step (5), the reaction temperature is 0.25-20 h.

In another preferred embodiment, in the step (5), the solvent in the reaction is selected from the groups consisting of tetrahydrofuran, dichloromethane, ethyl acetate, acetone, or the combinations thereof.

In another preferred embodiment, in the step (5), the molar ratio of the compound of formula 4 to the compound of formula Ia is 1/0.8~1/2.

In another preferred embodiment, the compound of formula 4 is prepared by the following step (4):

(4) reacting a compound of formula 3 a halogenated reagent to provide the compound of formula 4.

In the above formula, the R is defined as above; X is selected from Cl or Br.

The halogenated reagent is selected from the group consisting of phosphorus oxychloride, thionyl chloride, phosphorus trichloride, phosphorus pentachloride, phosphorus oxybromide, phosphorus tribromide, phosphorus pentabromide or combinations thereof; preferably phosphorus oxychloride.

In another preferred embodiment, in the step (4), the reaction is carried out under heating conditions; preferably, the reaction temperature is 50-200° C.

In another preferred embodiment, in the step (4), the reaction can be carried out with or without the presence of a reaction solvent, the reaction solvent has no special restriction, as long as it does not interfere with the reaction, and, for example, is selected from one or more of dichloromethane, dimethyl sulfoxide, tetrahydrofuran, benzene, toluene, chloroform, xylene, N, N-methyl formamide, N, N-dimethyl acetamide.

In another preferred embodiment, in the step (4), the reaction can be carried out in the presence of a base catalyst selected from the group consisting of N-ethyldiisopropylamine (DIPEA), triethylamine (Et₃N), N,N-Dimethylaniline, N,N-Diethylaniline, or the combinations thereof; preferably DIPEA.

In another preferred embodiment, in the step (4), the weight ratio of compound of the formula 3 to the halogenated reagent is 1:2-1:10.

In another preferred embodiment, in the method, the compound of formula 3 is prepared by the step (3):

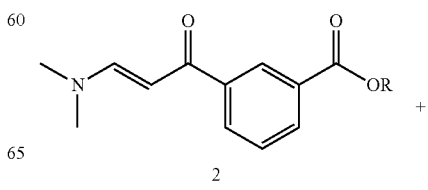

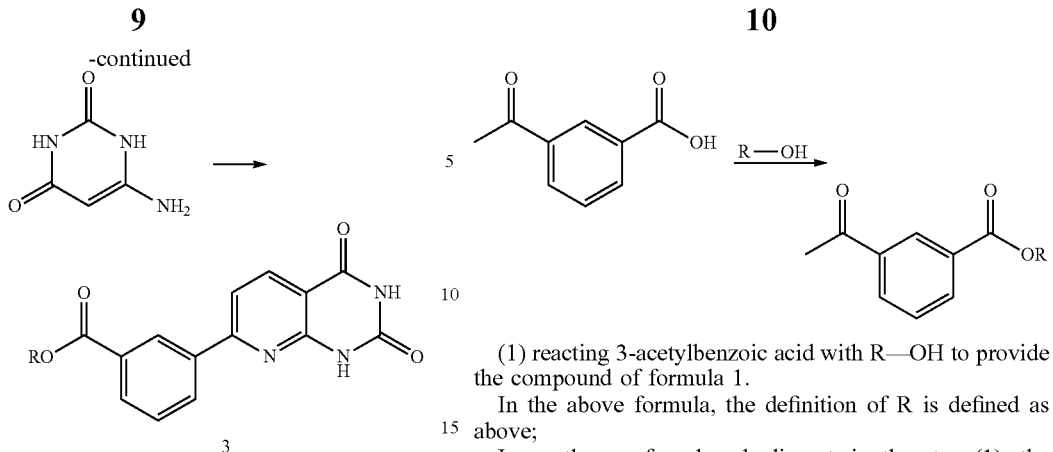

(3) reacting a compound of formula 2 with 6-aminouracil to provide the compound of formula 3.

In the above formula, the R is defined as above;

In another preferred embodiment, in the step (3), the reaction temperature is 50-200° C.

In another preferred embodiment, in the step (3), the reaction time is 2-48 h.

In another preferred embodiment, in the step (3), the reaction is carried out in a solvent selected from the group consisting of acetic acid, water, or the combinations thereof, preferably an acetic acid/water mixture solvent with acetic acid/water=1/1~2/1.

In another preferred embodiment, in the step (3), the molar ratio of the compound of formula 2 to 6-aminouracil is 1/1~1/1.5.

In another preferred embodiment, in the method, the compound of formula 2 is prepared by the step (2):

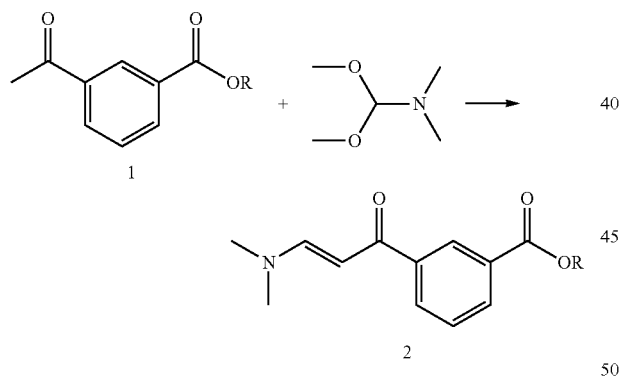

(2) reacting a compound of formula 1 with DMF-DMA in an inert solvent to provide the compound of formula 2.

In the above formula, the R is defined as above;

In another preferred embodiment, in the step (2), the reaction temperature is 50-150° C.

In another preferred embodiment, in the step (2), the reaction time is 2-12 h.

In another preferred embodiment, in the step (2), the reaction solvent is selected from the group consisting of DMF-DMA, DMF, toluene, xylene, or the combinations thereof; preferably DMF-DMA.

In another preferred embodiment, in the step (2), the weight ratio of the compound of formula 1 to DMF-DMA is 1:1~1:5.

In another preferred embodiment, the compound of formula 1 is prepared by the following method:

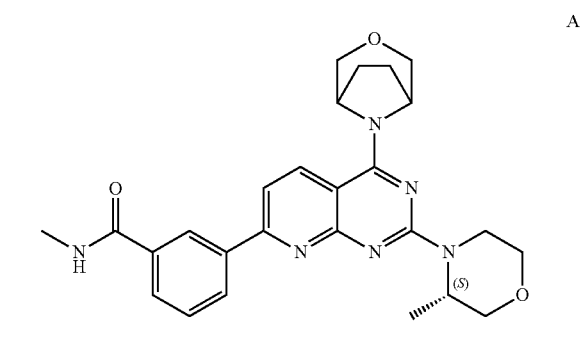

(1) reacting 3-acetylbenzoic acid with R—OH to provide the compound of formula 1.

In the above formula, the definition of R is defined as above;

In another preferred embodiment, in the step (1), the reaction was carried out in the presence of a catalyst; preferably, the catalyst is selected from the group consisting of concentrated sulfuric acid, thionyl chloride, or the combinations thereof; preferably concentrated sulfuric acid.

In another preferred embodiment, in the step (1), the reaction temperature is 50-120° C.

In another preferred embodiment, in the step (1), the reaction time is 1-24 h.

In another preferred embodiment, in the step (1), the reaction is carried out in a solvent selected from the group consisting of methanol, ethanol, propanol, butanol, or the combinations thereof; preferably methanol or ethanol.

In another preferred embodiment, in the step (1), the weight ratio of the compound of formula 1 to R—OH is 1/20~1/200.

In another preferred embodiment, the R—OH is methanol or ethanol.

In the second aspect of the invention, a method for preparing a compound of formula A is provided:

comprising the step:

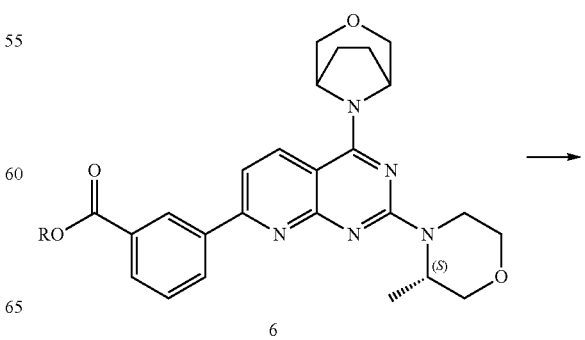

-continued

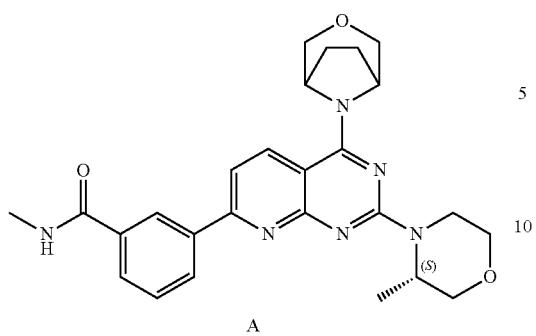

A (7a) reacting a compound of formula 6 with methylamine to provide the compound of formula A;

wherein, R is defined as above.

In the third aspect of the invention, a method for preparing compound of formula 6 is provided. The method comprises the steps:

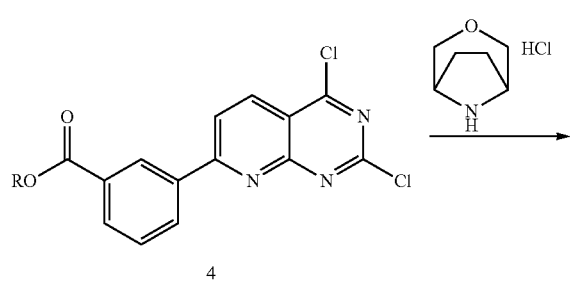

4

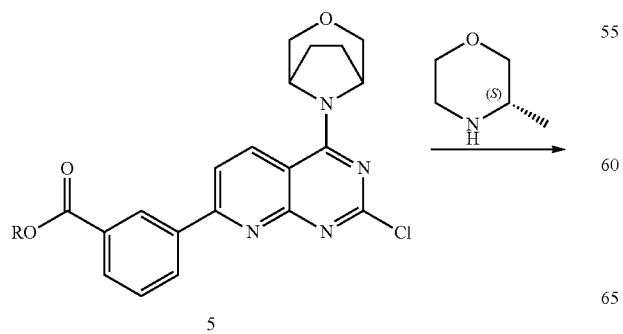

5

(5a) reacting a compound of formula 4 with 3-oxa-8-azabicyclo[3.2.1]octane hydrochloride in an inert solvent to provide a compound of formula 5;

-continued

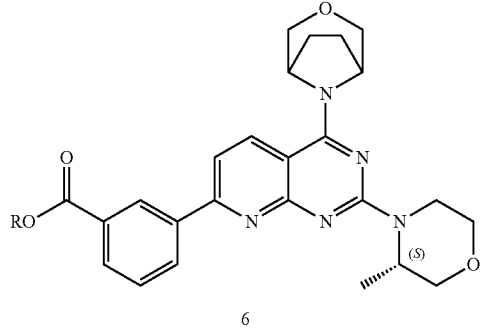

6

(6a) reacting the compound of formula 5 with 3-(S)-3-methylmorpholine in an inert solvent to provide the compound of formula 6;

In another preferred embodiment, in the step (5a), the reaction is carried out in the presence of a organic base catalyst; preferably, the organic base catalyst is selected from the group consisting of diisopropylethylamine, N,N-dimethylaniline, or the combinations thereof, preferably diisopropylethylamine.

In another preferred embodiment, in the step (5a), the reaction temperature is 0-80° C., preferably 10-50° C.

In another preferred embodiment, in the step (5a), the reaction temperature is 0.25-20 h.

In another preferred embodiment, in the step (5a), the solvent in the reaction is selected from the groups consisting of tetrahydrofuran, dichloromethane, ethyl acetate, acetone, or the combinations thereof.

In another preferred embodiment, in the step (5a), the molar ratio of the compound of formula 4 to 3-oxa-8-azabicyclo[3.2.1]octane Hydrochloride is 1/0.8~1/2.

In another preferred embodiment, in the step (6a), the reaction is carried out in the presence of an organic base catalyst; preferably, the organic base catalyst is selected from the group consisting of diisopropylethylamine, N,N-dimethylaniline, or the combinations thereof, preferably diisopropylethylamine.

In another preferred embodiment, in the step (6a), the reaction temperature is 80-180° C.

In another preferred embodiment, in the step (6a), the reaction temperature is 12-40 h.

In another preferred embodiment, in the step (6a), the solvent in the reaction is selected from the groups consisting of NMP, acetonitrile, toluene, 1,4-dioxane, DMF, xylene, or the combinations thereof.

In another preferred embodiment, in the step (6a), the molar ratio of the compound of formula I to 3-(S)-3-methylmorpholine is 1/1~1/1.5.

The fourth aspect of the invention, a method for preparing a compound of formula B is provided.

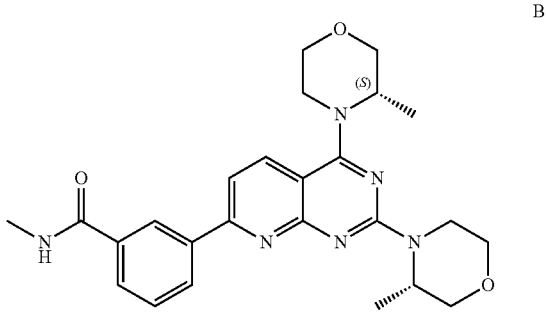

B

The method comprises the step:

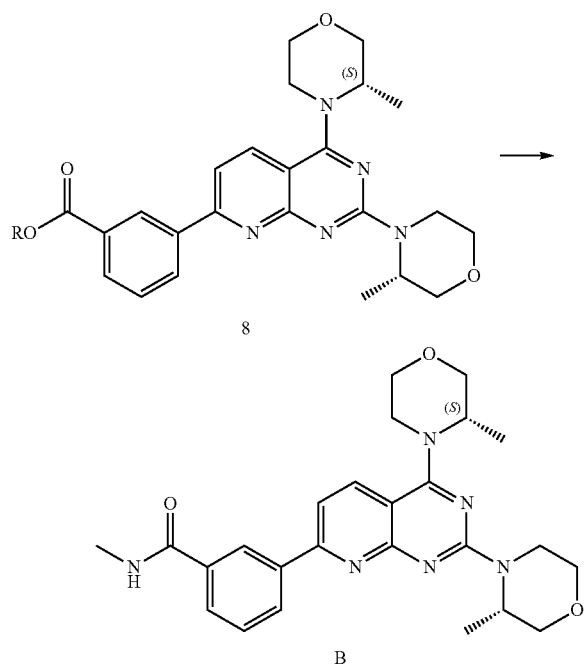

(7b) reacting a compound of formula 8 with methylamine to provide the compound of formula B;
wherein, R is defined as above.

DETAILED DESCRIPTION

Upon extensive and intensive studies, the inventors have finally determined to preparing the intermediate formula 4 from starting material 3-acetylbenzoic acid, thus obtaining a novel process of synthesizing a substituted pyridine and pyrimidine compound by comparing the three synthetic routes. The synthetic method has advantages such as high yield, pure product and suitable for industrial production, therefore, it is very suitable for the production of substituted pyridine and pyrimidine compound such as those disclosed in Chinese Patent No. 201310068888.8. Based on the above findings, the inventors have completed the invention.

Terms

As used herein, the term "a compound of formula 4" and "intermediate(4)" can be used interchangeably to refer the compound described as following structure in the invention:

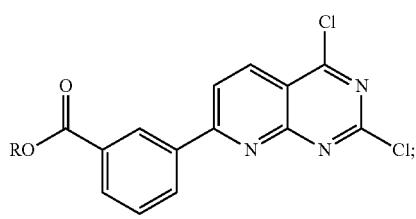

wherein, R is selected from the group consisting of $C_1$-$C_4$ alkyl, preferably methyl or ethyl.

The term "$C_1$-$C_4$ alkyl" refers to a linear or branched chain alkyl with 1 to 4 carbon atoms, typical examples include methyl, ethyl, isopropyl, n-butyl, iso-butyl, sec-butyl, tert-butyl, etc.

The term "$C_1$-$C_4$ alkoxy" refers to a linear or branched chain alkoxy with 1 to 4 carbon atoms, typical examples include methoxy, ethoxy, propoxy, isopropoxy and butoxy, etc.

The term "$C_1$-$C_4$ ester group" refers to a group with a "—COO—$C_1$-$C_4$ alkyl" structure or a "—OC(O)—$C_1$-$C_4$ alkyl" structure.

In the invention, the term "heterocycle" comprises aliphatic heterocycles and aromatic heterocycles with 3 to 10 carbon atoms, or fused polycycle or unfused polycycle such as single ring, bicyclo ring, spiro ring or bridged ring which comprises 1-3 hetero atoms as ring members, in which the hetero atom refers to nitrogen, oxygen or sulphur atom.

In the invention, the term "substitution" refers to one or more substituents on the group are substituted with substituents selected from the group consisting of halogen, $C_1$-$C_6$ alkyl, $C_1$-$C_4$ alkoxy, hydroxy, amino, carboxyl, nitro, cyano.

The synthesis of Compound A and Compound B is not suitable for industrial production in the published literature such as Chinese Patent (201310068888.8), Bioorganic & Medicinal Chemistry Letters 23 (2013) 1212-1216. The invention discloses a simple synthetic method for the synthesis of such compounds.

By comparing the structures of Compounds A and B, it is found that both compounds contain a common methylbenzamide structural fragment which can be introduced from the starting material or from introducing potential groups to convert to amides, thereby providing three routes, of which the specific routes are as follows:

Synthesis route 1, the formamide group is introduced from the starting material

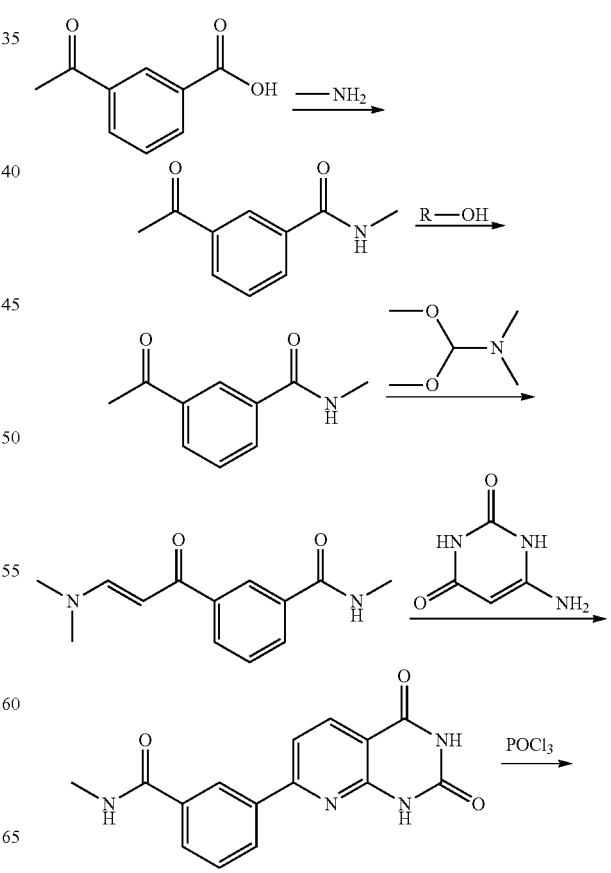

15
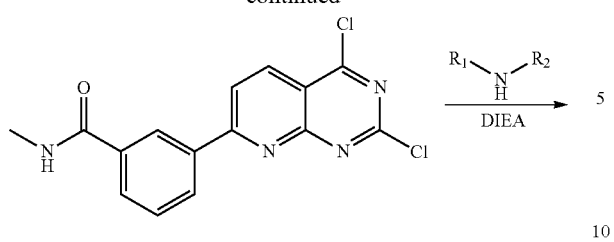
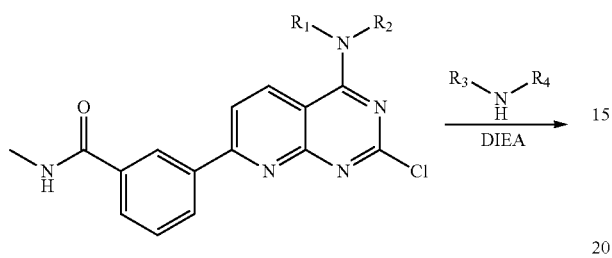
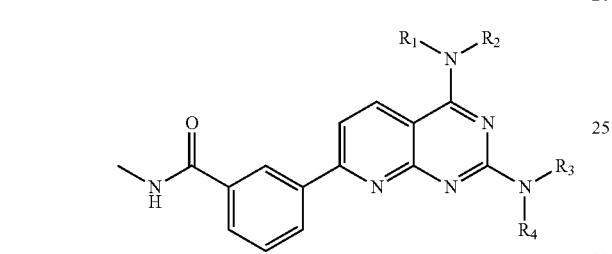
when $R_1\text{-NH-}R_2$ = 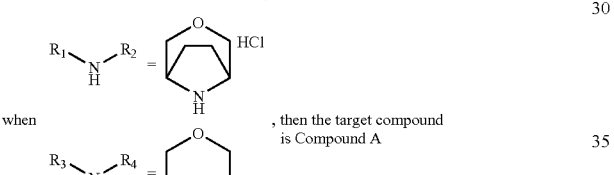, then the target compound is Compound A
$R_3\text{-NH-}R_4$ =
when $R_1\text{-NH-}R_2$ = 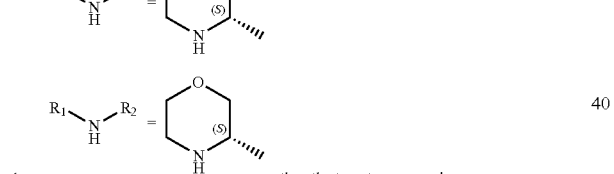, then the target compound is Compound B
$R_3\text{-NH-}R_4$ =
Synthesis route 2, converting cyano into amide:
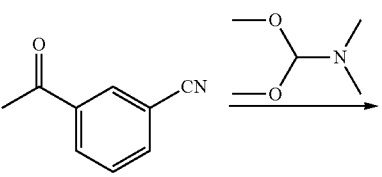
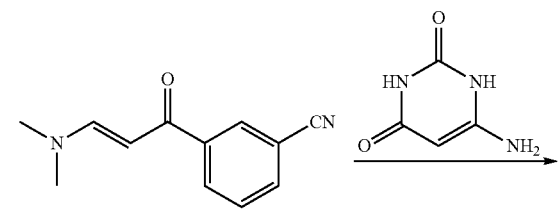
16
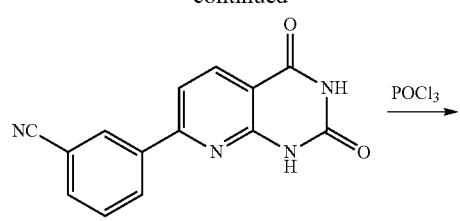
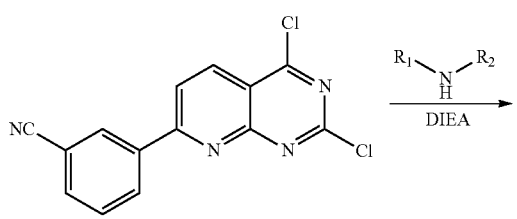
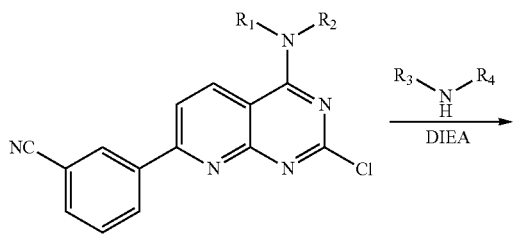
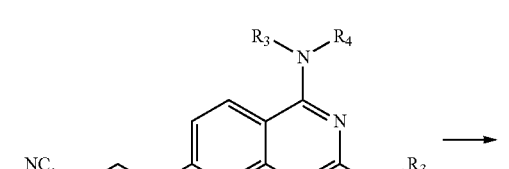
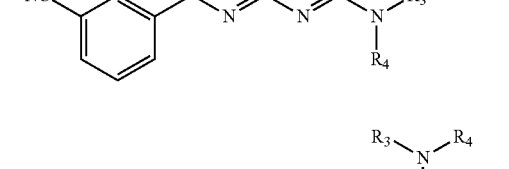
when $R_1\text{-NH-}R_2$ = 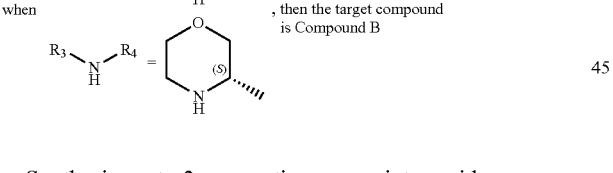, then the target compound is Compound A
$R_3\text{-NH-}R_4$ =
when $R_1\text{-NH-}R_2$ = 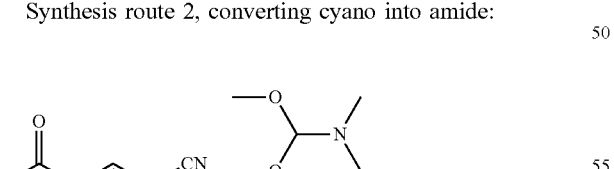, then the target compound is Compound B
$R_3\text{-NH-}R_4$ =

Synthesis route 3, converting carboxyl into amide:

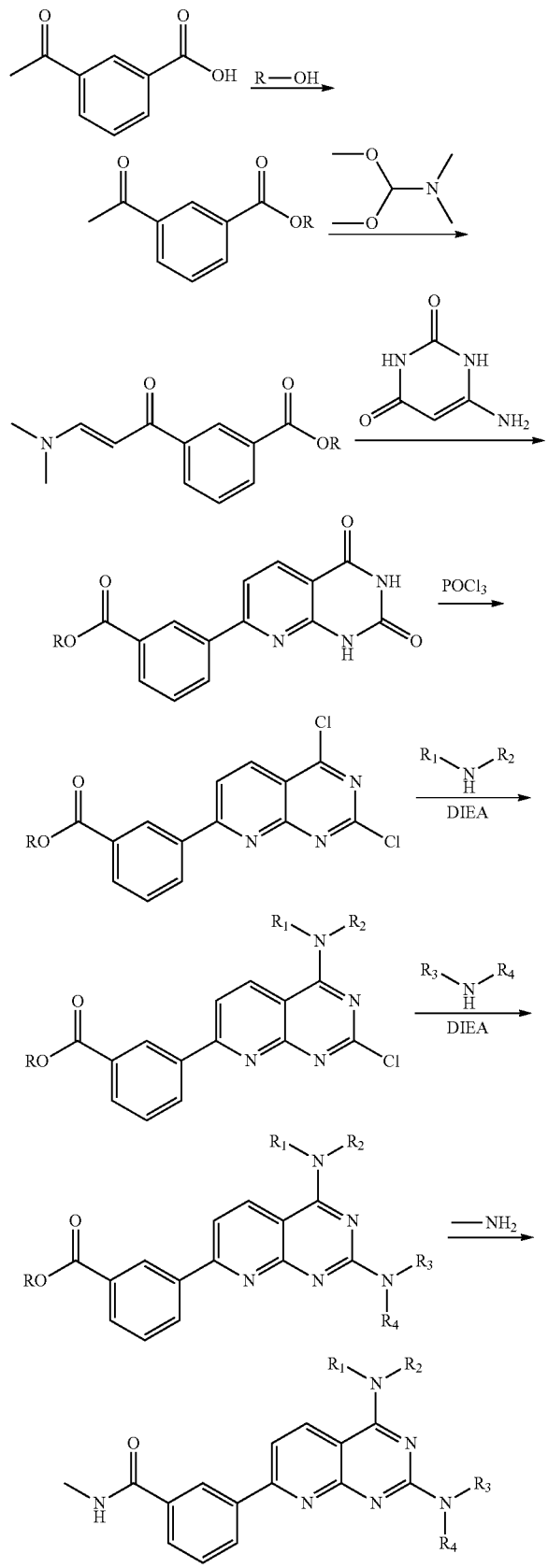

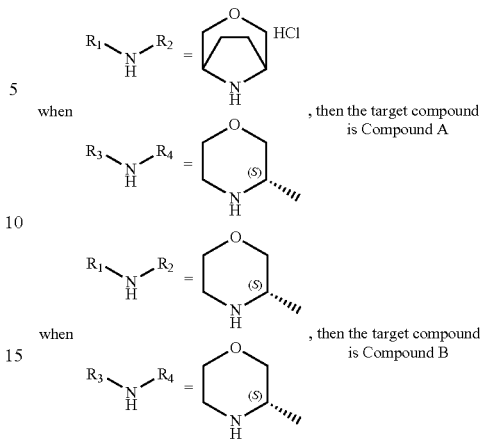

when ... then the target compound is Compound A when ... then the target compound is Compound B By comparing the reaction conditions, by-products, product properties, yield and other factors, synthetic routes 3 is chosen finally.

Preparation of Intermediate 4 Compound (Intermediate (4))

The common intermediate of Compound A and Compound B is intermediate (4):

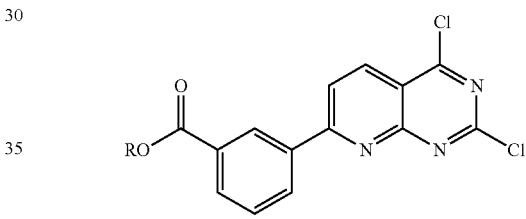

wherein R is selected from the group consisting of $C_1$-$C_4$ alkyl, preferably methyl or ethyl.

Preferably, the method for preparing the intermediate compound of formula 4 comprises the steps:

The starting material 3-acetylbenzoic acid is mixed with methanol or ethanol, sulfuric acid or thionyl chloride is added to the resulting solution, and the mixture was heated to reflux to form intermediate 1; and the intermediate 1 is heated to react with DMF-DMA to form intermediate 2, of which the reaction solvent can be DMF-DMA itself, DMF, toluene, xylene; and the intermediate 2 is heated to react with 6-aminouracil to form intermediate 3, of which the reaction solvent is acetic acid and water mixture solvent; the intermediate 3 and phosphorus oxychloride are heated to reflux to form intermediate 4, the organic base used to promote chlorination reaction is one of diisopropylethylamine (DIPEA), N, N-dimethylaniline.

The Synthesis Step of Compound A

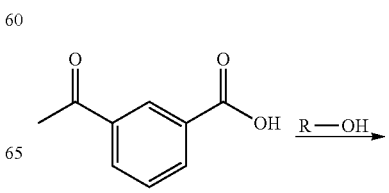

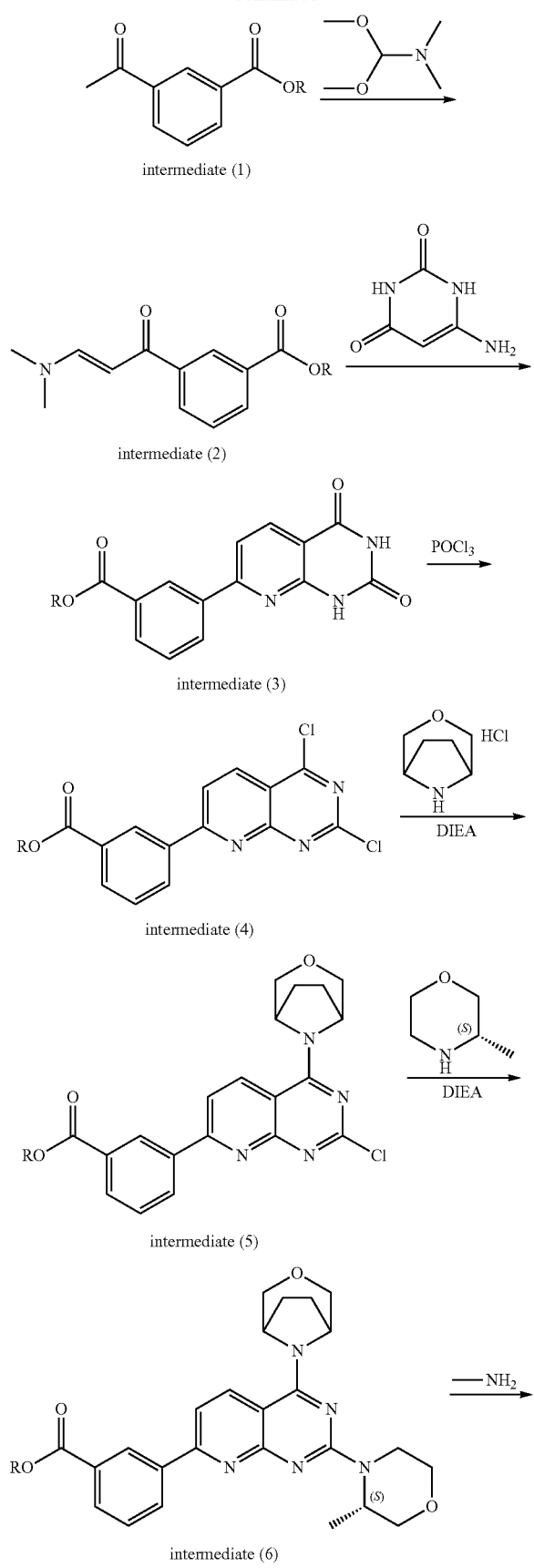

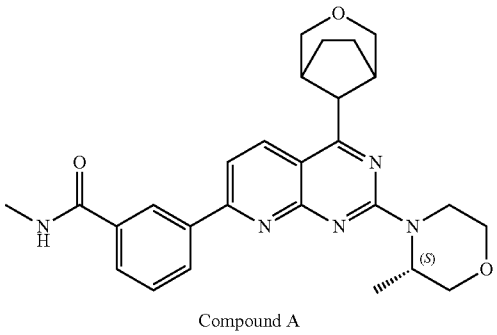

Compound A

The method for preparing Compound A as provided herein starts from the intermediate 4. Firstly, the intermediate 4 is reacted with 3-oxa-8-azabicyclo[3.2.1]octane to form intermediate 5, in which the reaction solvent is one of tetrahydrofuran, dichloromethane, ethyl acetate and acetone, the base is DIPEA or triethylamine; and the intermediate 5 is reacted with 3-(S)-3-methylmorpholine to form the intermediate 6, of which the solvent is one of acetonitrile, toluene, 1,4-dioxane, DMF, xylene. The intermediate 6, methanol alcoholic solution and base are heated to react to form Compound A.

The Synthesis Step of Compound B

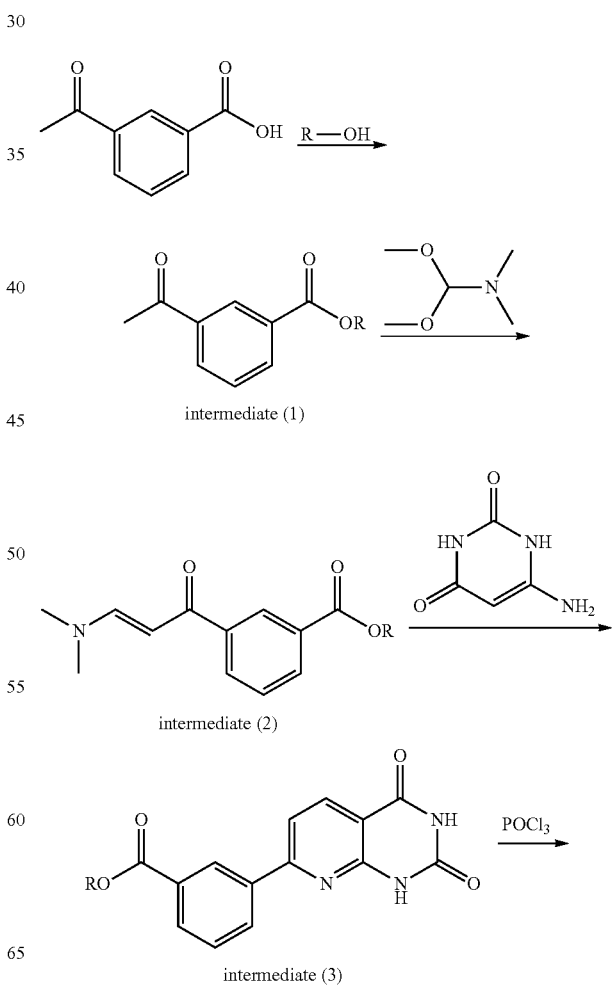

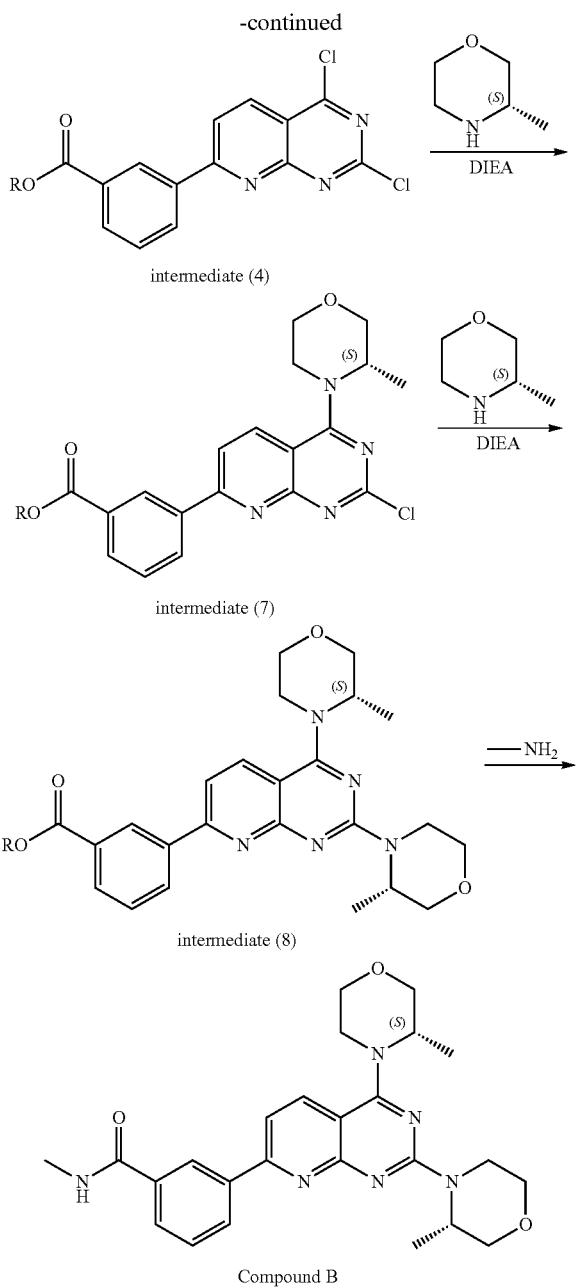

intermediate (4)

intermediate (7)

intermediate (8)

Compound B

The method for preparing Compound B as provided herein starts from intermediate 4. Firstly, the intermediate 4 is reacted with 3-(S)-3-methylmorpholine to form intermediate 7, of which the reaction solvent is one of tetrahydrofuran, dichloromethane, ethyl acetate and acetone, the base was DIPEA or triethylamine; and the intermediate 7 is reacted with 3-(S)-3-methylmorpholine to form the intermediate 8, the solvent is one of acetonitrile, toluene, 1,4-dioxane, DMF, xylene. The intermediate 8, methanol alcoholic solution and base were reacted under heating condition to form Compound B.

The Main Merits of the Present Invention Comprise:

(1) Compared with the routes in the prior art, the invention has advantages such as easy operation, mild condition, less environmental pollution, simple synthesis process, convenient raw material acquisition, high yield, and suitable for industrial production (2) Compared with reacting with an aminated intermediate and then preparing the compound of formula III, the product prepared by the method herein is of higher purity and can be readily separated, and is therefore more suitable for industrial production.

The compounds obtained by the method were identified by 1H-NMR and MS, and were consistent with the theoretical values.

The present invention will be further illustrated below with reference to the specific examples. It should be understood that these examples are only to illustrate the invention but not to limit the scope of the invention. The experimental methods with no specific conditions described in the following examples are generally performed under the conventional conditions or according to the manufacture's instructions. Unless otherwise stated, the percentages and parts are calculated by weight.

EXAMPLE 1 THE SYNTHESIS OF COMPOUND A

Step (1) Esterification Reaction 3-acetylbenzoic acid (200 g) was dissolved in 2 L methanol (or ethanol, propanol) and 128 ml concentrated sulfuric acid was slowly added at room temperature. The mixture was heated to reflux overnight. After the reaction was completed, the methanol was removed by concentration under reduced pressure. The remaining oil was dissolved in 2 L ethyl acetate and washed with 1 L water for once, 1 L saturated sodium bicarbonate for twice, and 0.5 L saturated brine for once. The organic phase was dried by using anhydrous sodium sulfate and the ethyl acetate was removed by concentration under reduced pressure to obtain a red oil, cooled at room temperature to obtain yellow solid (189 g), yield: 87%, $^1$H NMR (400 MHz, Chloroform-d) 8.58 m, 1H), 8.30-8.18 (m, 2H), 7.60-7.54 (m, 1H), 3.96 (s, 3H), 2.66 (s, 3H).

Step (2) Condensation Reaction

Intermediate (1) (195 g) was dissolved in toluene (1 L), DMF-DMA (195 ml) was added and the solution was heated to reflux for 6 hours. After the reaction was completely completed, the reaction was concentrated under reduced pressure to remove the solvent to form a brown oil. 400 ml methyl tert-butyl ether was added, filtered and dried under reduced pressure to obtain 191 g yellow solid, yield 75%. $^1$H NMR (400 MHz, Chloroform-d) δ 8.54-8.51 (m, 1H), 8.15-8.10 (m, 2H), 7.84 (d, J=12.3 Hz, 1H), 7.53-7.47 (m, 1H), 5.75 (d, J=12.3 Hz, 1H), 3.94 (s, 3H), 3.17 (s, 3H), 2.96 (s, 3H). LRMS calcd for C13H16NO3 ([M+H]+): 234.11, found: 234.08.

Step (3) Cyclization Reaction

6-Aminouracil (109 g) was dissolved in 2.5 L acetic acid, and intermediate (2) (167 g) was added to the system in batches and heated to 100° C. with stirring for 12 hours. After the reaction was completely completed, the mixed solvent was removed under reduced pressure. The pH was adjusted to 7 with 2N potassium hydroxide aqueous solution and filtered. The solid was stirred in 400 ml saturated citric acid aqueous solution (1.5 L) for 1 hour, and filtered and the filter cake was washed with water to neutral to obtain 204 g yellow powder. Yield: 95.8%. $^1$H NMR (400 MHz, DMSO-d6) δ 11.79 (s, 1H), 11.49 (s, 1H), 8.75-8.72 (m, 1H), 8.43-8.37 (m, 1H), 8.35 (d, J=8.1 Hz, 1H), 8.12-8.07 (m, 1H), 7.89 (d, J=8.1 Hz, 1H), 7.71 (t, J=7.8 Hz, 1H), 3.91 (s, 3H). LRMS calcd for $C_{15}H_{12}N_3O_4$ ([M+H]$^+$): 298.08, found: 298.11.

Step (4) Chlorination Reaction

Intermediate (3) (200 g) was dissolved in 3 L phosphorus oxychloride and heated to 120° C. to reflux for 18 hours. After the reaction was completely completed, the solvent was evaporated, and ethyl acetate (2 L) was added for pulping, filtered, the residual solvent was removed under reduced pressure to obtain flocculent solid (202 g). yield: 90.9%. $^1$H NMR (400 MHz, Chloroform-d) δ 8.92-8.90 (m, 1H), 8.68 (d, J=8.7 Hz, 2H), 8.62-8.57 (m, 1H), 8.26 (d, J=8.7 Hz, 1H), 7.70-7.65 (m, 1H), 3.99 (s, 3H). LRMS calcd for $C_{15}H_{10}Cl_2N_3O_2$ ([M+H]$^+$): 334.01, found: 334.13.

Step (5) Substitution Reaction 1

Intermediate (4) (100 g) was dissolved in tetrahydrofuran (4 L), and bridged morpholine hydrochloride (53.7 g) and DIEA (152 ml) were added, and the mixture was stirred at room temperature for 3 hours. After the reaction was completely completed, the reaction solution was evaporated to obtain a red solid, 2 L ethyl acetate was added for pulping, filtered. The residual solvent was removed under reduced pressure to obtain reddish solid (113 g). yield: 91.5%.

The intermediate (4), bridged morpholine hydrochloride, solvent, temperature and time were changed as follows, and other conditions remain unchanged. The results were as follows:

| experiment | intermediate (4) (g) | bridged morpholine hydrochloride (g) | solvent | temperature | time | results |
|---|---|---|---|---|---|---|
| 1 | 1 (1.0 eq) | 0.675 (1.5 eq) | Tetrahydrofuran 30 mL | 20° C.-25° C. | 3 hours | Obtained 1 g product, yield: 81% |
| 2 | 1 (1.0 eq) | 0.448 (1.0 eq) | Tetrahydrofuran 30 mL | 20° C.-25° C. | 20 hours | Obtained 1 g product, yield: 81% |
| 3 | 1 (1.0 eq) | 0.54 (1.2 eq) | Tetrahydrofuran 30 mL | 20° C.-25° C. | 2.5 hours | Obtained 1.1 g product, yield: 89% |
| 4 | 1 (1.0 eq) | 0.336 (0.8 eq) | Tetrahydrofuran 30 mL | 20° C.-25° C. | 20 hours | Obtained 1 g product, yield: 81% |
| 5 | 0.5 (1.0 eq) | 0.275 (1.2 eq) | Tetrahydrofuran 15 mL | 45° C.-50° C. | 3.5 hours | Obtained 0.5 g product, yield: 81% |
| 6 | 0.5 (1.0 eq) | 0.275 (1.2 eq) | tetrahydrofuran 15 mL | 0° C.-5° C. | 3.5 hours | Obtained 0.45 g product, yield: 73% |
| 7 | 0.5 (1.0 eq) | 0.275 (1.2 eq) | Tetrahydrofuran 15 mL | 70° C.-80° C. | 15 minutes | Obtained 0.5 g product, yield: 81% |
| 8 | 0.5 (1.0 eq) | 0.275 (1.2 eq) | ethyl acetate 15 mL | 20° C.-25° C. | 4 hours | Obtained 0.5 g product, yield: 81% |
| 9 | 0.5 (1.0 eq) | 0.275 (1.2 eq) | acetone 15 mL | 20° C.-25° C. | 4 hours | Obtained 0.47 g product, yield: 76% |
| 10 | 0.5 (1.0 eq) | 0.275 (1.2 eq) | dichloromethane 15 mL | 20° C.-25° C. | 2 hours | Obtained 0.5 g product, yield: 81% |
| 11 | 45 (1.0 eq) | 24.18 (1.2 eq) | dichloromethane 15 mL | 20° C.-25° C. | 2.5 hours | Obtained 50 g product, yield: 82% |
| 12 | 0.5 (1.0 eq) | 0.275 (1.2 eq) | Dichloromethane 15 mL | 40° C.-50° C. | 1.5 hours | Obtained 0.5 g product, yield: 81% |
| 13 | 197 (1.0 eq) | 105.8 (1.2 eq) | dichloromethane 4500 mL | 20° C.-25° C. | 3 hours | Obtained 222 g product, yield 92% |

The data of the intermediate (5) was as follows:

$^1$H NMR (400 MHz, Chloroform-d) δ 8.87-8.85 (m, 1H), 8.56-8.53 (m, 1H), 8.30 (d, J=8.7 Hz, 1H), 8.20-8.17 (m, 1H), 7.91 (d, J=8.7 Hz, 1H), 7.62 (t, J=7.8 Hz, 1H), 4.87 (s, 2H), 4.01 (d, J=11.0 Hz, 2H), 3.97 (s, 3H), 3.86-3.79 (m, 2H), 2.26-1.97 (m, 4H). LRMS calcd for $C_{21}H_{20}ClN_4O_3$ ([M+H]$^+$): 411.12, found: 411.22.

Step (6) Substitution Reaction 2

Intermediate(5) (50 g) was dissolved in 1.5 L DMF, DIEA (31.5 g) and 3-S-methylmorpholine (18.5 g) were successively added and heated at 140° C. to reflux for 24 hours. and cooled to room temperature. The solvent was removed by concentration under reduced pressure, dissolved in 3 L ethyl acetate, washed with 2000 ml water for twice, 1000 ml saturated brine for twice, and dried with anhydrous sodium sulfate and concentrated under reduced pressure to obatin a yellow solid crude product. The crude product was added to 300 ml ethyl acetate for pulping, filtered and dried under reduced pressure to obtain 41 g yellow solid. Yield: 70.7%.

The intermediate (5), bridged morpholine hydrochloride, solvent, temperature and time were changed as follows, and other conditions remain unchanged. The results were as follows.

| experiment | intermediate (5) (g) | 3-S-Methyl-morpholine (g) | DIEA (g) | solvent | temperature | time | results |
|---|---|---|---|---|---|---|---|
| 1 | 1 (1.0 eq) | 0.363 (1.5 eq) | 0.259 (2.0 eq) | xylene/30 mL | 140-145° C. | 24 hours | Obtained 1 g product, yield: 86.2% |
| 2 | 0.411 (1.0 eq) | 0.152 (1.5 eq) | 0.259 (2.0 eq) | acetonitrile 30 mL | 80-85° C. | 40 hours | Obtained 0.4 g product, yield: 83.9% |
| 3 | 0.411 (1.0 eq) | 0.152 (1.5 eq) | 0.259 (2.0 eq) | toluene 30 mL | 110-115° C. | 40 hours | Obtained 0.4 g product, yield: 83.9% |
| 4 | 0.411 (1.0 eq) | 0.152 (1.5 eq) | 0.259 (2.0 eq) | dioxane 30 mL | 100-105° C. | 40 hours | Obtained 0.4 g product, yield: 83.9% |
| 5 | 0.411 (1.0 eq) | 0.152 (1.5 eq) | 0.259 (2.0 eq) | DMF 30 mL | 140-145° C. | 23 hours | Obtained 0.4 g product, yield: 86% |
| 6 | 1 (1.0 eq) | 0.246 (1.0 eq) | 0.629 (2.0 eq) | xylene/30 mL | 140-145° C. | 27 hours | Obtained 1 g product, yield: 86.2% |
| 7 | 1 (1.0 eq) | 0.259 (1.05 eq) | 0.629 (2.0 eq) | xylene/30 mL | 140-145° C. | 27 hours | Obtained 1 g product, yield: 86.2% |
| 8 | 1 (1.0 eq) | 0.271 (1.1 eq) | 0.629 (2.0 eq) | xylene/30 mL | 140-145° C. | 27 hours | Obtained 1 g product, yield: 86.2% |
| 9 | 1 (1.0 eq) | 0.295 (1.2 eq) | 0.629 (2.0 eq) | xylene/30 mL | 140-145° C. | 27 hours | obtained 0.9 g product, yield: 78% |
| 10 | 1 (1.0 eq) | 0.370 (1.5 eq) | 0.629 (2.0 eq) | xylene/30 mL | 80-85° C. | 18 hours | obtained 0.9 g product, yield: 78% |
| 11 | 1 (1.0 eq) | 0.370 (1.5 eq) | 0.629 (2.0 eq) | xylene/30 mL | 110-115° C. | 18 hours | Obtained 1 g product, yield: 86.2% |
| 12 | 1 (1.0 eq) | 0.370 (1.5 eq) | 0.629 (2.0 eq) | xylene/30 mL | 140-145° C. | 18 hours | obtained 0.9 g product, yield: 78% |
| 13 | 30 (1.0 eq) | 11.1 (1.5 eq) | 18.9 (2.0 eq) | xylene/900 mL | 140-145° C. | 20 hours | obtained 28 g product, yield: 80% |
| 14 | 1 (1.0 eq) | 0.370 (1.5 eq) | 0.629 (2.0 eq) | xylene/30 mL | 140-145° C. | 38 hours | obtained 0.9 g product, yield: 78% |

| experiment | intermediate (5) (g) | 3-S-Methyl-morpholine (g) | DIEA (g) | solvent | temperature | time | results |
|---|---|---|---|---|---|---|---|
| 15 | 1 (1.0 eq) | 0.370 (1.5 eq) | potassium carbonate 0.672 g (2.0 eq) | NMP 30 mL | 140-145° C. | 16 hours | Obtained 1 g product, yield: 86.2% |

The data of the intermediate (6) was described as follows:
$^1$H NMR (400 MHz, Chloroform-d) δ 8.77-8.75 (m, 1H), 8.47-8.43 (m, 1H), 8.13 (d, J=8.2 Hz, 2H), 7.64-7.49 (m, 2H), 4.93 (s, 1H), 4.73-4.45 (m, 3H), 4.09-3.97 (m, 3H), 3.96 (s, 3H), 3.83-3.69 (m, 4H), 3.56 (td, J=11.8, 2.8 Hz, 1H), 3.38 (td, J=13.0, 3.7 Hz, 1H), 2.22-1.90 (m, 4H), 1.36 (d, J=6.8 Hz, 3H). LRMS calcd for $C_{26}H_{30}N_5O_4$ ([M+H]$^+$): 476.23, found: 476.33.

Step (7) Ammonolysis Reaction
Step (7.1) Amidation Reaction (Amination Method)

Intermediate (6)(40 g) was dissolved in 30% methanol solution (1100 ml) and heated at 40-45° C. to react for 22 hours. After the reaction was completed, the solvent was removed by concentration under reduced pressure. The residue was added to 2 L dichloromethane, washed with 500 ml water for three times, 500 ml saturated brine for once, and the organic layer was dried with anhydrous sodium sulfate, concentrated under reduced pressure. The solid was added with 400 ml ethyl acetate for pulping, filtered and dried to obtain Compound A (36 g). Yield: 90.1%, purity: 99.7%.

Step (7.2) Amidation Reaction (Acyl Chloride Method)

Intermediate (6) (40 g) was dissolved in 1 L methanol, 2N sodium hydroxide solution (17 g) was added and stirred at room temperature for 1 hour. After the reaction was completed, the solvent was removed under reduced pressure, dissolved in 2 L dichloromethane, neutralized with 1N hydrochloric acid, and the organic phase was washed once with 500 ml saturated brine. The organic layer was dried with anhydrous sodium sulfate, and concentrated under reduced pressure to obtain 38 g yellow solid. The intermediate was dissolved in 2 L dichloromethane, and N, N-dimethylformamide (0.5 ml) was added. Diisopropylethylamine (21.5 ml) was added and oxalyl chloride (10.6 ml) was slowly added dropwise under ice bath, the system was moved to room temperature to react for 8 hours. After the reaction was completed, the solvent was evaporated, and the intermediate was dissolved in 1 L anhydrous dichloromethane. Diisopropylethylamine (43 ml) and methylamine hydrochloride (8.3 g) were added, and stirred for 6 hours at room temperature. After the reaction was completed, the solvent was removed under reduced pressure. The residue was added to 2 L dichloromethane, washed with 500 ml water for three times, 500 ml saturated brine for once, and the organic layer was dried by using anhydrous sodium sulfate, concentrated under reduced pressure. The solid was added with 400 ml ethyl acetate and pulped, filtered and dried to obtain Compound A (34 g), yield: 85.2%.

Step (7.3) Amidation Reaction (Active Ester Method)

Intermediate (6) (40 g) was dissolved in 500 mL methanol, 2N sodium hydroxide solution (17 g) was added, stirred for 1 hours at room temperature. When the reaction was completely completed, the solvent was removed under reduced pressure, dissolved in 2 L dichloromethane, neutralized with 1N hydrochloric acid, and the organic phase was washed once with 500 ml saturated brine. The organic layer was dried with anhydrous sodium sulfate, and concentrated under reduced pressure to obtain 38 g yellow solid. This intermediate was dissolved in anhydrous dichloromethane, and N, N-dimethylformamide (0.5 ml), diisopropylethylamine (43 ml), EDCI (18.9 g), HOBT (13.4 g) and N-hydroxysuccinim reaction was completed, the solvent was evaporated, and the intermediate was dissolved in 2 L dichloromethane, washed with 500 ml water for three times, 500 ml saturated sodium bicarbonate solution for once, and 500 ml saturated salt for once, dried with anhydrous sodium sulfate and distillated to dry. The intermediate was dissolved in 1 L anhydrous dichloromethane, and diisopropylethylamine (43 ml) and methylamine hydrochloride (8.3 g) were added, stirred at room temperature for 6 hours. After the reaction was completed, the solvent was removed by concentration under reduced pressure, and the residual was added to 2 L dichloromethane, washed with 500 ml water for three times, 500 ml saturated saline for once, and the organic layer was dried with anhydrous sodium sulfate, concentrated under the reduced pressure. The solid was added with 400 ml ethyl acetate and pulped, filtered and dried to obtain Compound A (33 g), yield: 82.6%.

Step (7.4) Amidation Reaction (Direct Condensation Method)

Intermediate (6) (40 g) was dissolved in 500 mL methanol, 2N sodium hydroxide solution (17 g) was added, stirred at room temperature for one hour. After the reaction was completed, the solvent was removed by concentration under the reduced pressure, dissolved with 2 L dichloromethane, neutralized with 1N hydrochloric acid, and the organic phase was washed once with 500 ml saturated saline. The organic layer was dried with anhydrous sodium sulfate and concentrated under reduced pressure to gain 38 g yellow solid. This intermediate was dissolved in 2 L anhydrous dichloromethane, followed by adding diisopropylethylamine (72 ml), EDCI (18.9 g), HOBT (13.3 g) and methylamine hydrochloride (8.3 g) were added successively, and stirred at room temperature for 8 hours. After the reaction was completed, the solvent was removed by concentration under reduced pressure, the residue was added to 2 L dichloromethane, washed with 500 ml water for three times, 500 ml saturated sodium bicarbonate solution for once, and 500 ml saturated saline for once. The organic layer was dried with anhydrous sodium sulfate and concentrated under the reduced pressure. The solid was added with 400 ml ethyl acetate and pulped, filtered and dried to obtain Compound A (33.5 g), yield: 83.9%.

Data Characterization of Compound A $^1$H NMR (400 MHz, Chloroform-d) δ 8.61 (s, 1H), 8.25-8.18 (m, 1H), 8.12 (d, J=8.4 Hz, 1H), 8.00-7.92 (m, 1H), 7.65-7.46 (m, 2H), 6.55 (brs, 1H), 4.91 (s, 1H), 4.70-4.47 (m, 3H), 4.14-3.94 (m, 3H), 3.83-3.65 (m, 4H), 3.56 (m, 1H), 3.38 (td, J=12.9, 3.7 Hz, 1H), 3.05 (d, J=4.8

Hz, 3H), 2.20-1.92 (m, 4H), 1.35 (d, J=6.8 Hz, 3H). LRMS calcd for $C_{26}H_{31}N_6O_3$ ([M+H]$^+$): 475.25, found: 475.37.

EXAMPLE 2 THE SYNTHESIS OF COMPOUND B

The synthesis of Compound B from the starting material to the step (4) is identical to the synthesis of the Compound A, and shares the intermediate (4) with the Compound A.

Step (5) Substitution Reaction 1

Intermediate (4) (100 g) in the example 1 is dissolved in tetrahydrofuran (2 L), 3-S-methylmorpholine hydrochloride (42.7 ml), and DIEA (109 ml) were added and stirred at room temperature for 3 hours. After the reaction was completed, the reaction mixture was dried to obtain red brown solid, ethyl acetate (1 L) was added for pulping, filtered, the solvent was removed under reduced pressure to obtain reddish solid (109 g), yield: 90.6%. LRMS calcd for $C_{20}H_{20}ClN_4O_3$ ([M+H]$^+$): 399.12, found: 399.22.

Step (6) Substitution Reaction 2

Intermediate (7) (50 g) was dissolved in 1.5 L DMF, DIEA (31.5 g) and 3-S-methylmorpholine (15.3 g) were added successively, and heated at 140° C. to reflux for 24 hours and cooled to room temperature. The solvent was removed by concentrated under reduced pressure, dissolved with 3 L ethyl acetate, washed with 2000 ml water for twice, 1000 ml saturated saline for once, dried with anhydrous sodium sulfate, concentrated under reduced pressure to obtain yellow solid products. The crude product was added with 300 ml ethyl acetate and pulped, suction filtrated, dried under reduced pressure to provide yellow solid (40 g), yield: 70.6%. LRMS calcd for $C_{25}H_{30}N_5O_4$ ([M+H]+): 464.23, found: 464.33.

Step (7) Ammonolysis Reaction

Step (7.1) Amidation Reaction (Ammonolysis Method)

Intermediate (8) (40 g) was dissolved in 30% methylamine alcohol solution (1100 ml), heated at 40-45° C. for 22 hours. After the reaction was completely completed, the solvent was removed by concentrated under reduced pressure, and the residual was added with 2 L dichloromethane, washed with 500 ml water for 3 times, 500 ml saturated saline for once, and the organic layer was dried with anhydrous sodium sulfate, concentrated under reduced pressure. The solid was added with 400 ml ethyl acetate and pulped, filtered and dried to obtain Compound B (37.2 g), yield: 90.2%, purity: 99.7%.

Step (7.2) Amidation Reaction (Acyl Chloride Method)

Intermediate (8) (40 g) was dissolved in 500 mL methanol, 2N sodium hydroxide solution (17.3 g) was added, stirred at room temperature for 1 hour. After the reaction was completed, the solvent was removed by concentration under reduced pressure, dissolved with 2 L dichloromethane, neutralized with 1N hydrochloric acid, and the organic phase was washed once with 500 ml saturated saline. The organic layer was dried with anhydrous sodium sulfate, concentrated under reduced pressure to obtain 36 g yellow solid. This intermediate was dissolved in 2 L anhydrous dichloromethane, N, N-dimethylformamide (0.5 ml) was added, diisopropylamine (20.9 ml) was added, and oxalyl chloride (10.6 ml) was slowly added dropwise in the ice bath. The system was moved to room temperature to react for 8 hours. The solvent was dried after the reaction was completed. The intermediate was dissolved in 1 L anhydrous dichloromethane, and diisopropylethylamine (43 ml) and methylamine hydrochloride (8.1 g) were added, stirred at room temperature for 6 hours. After the reaction was completed, the solvent was removed under reduced pressure, the residual was added to 2 L dichloromethane, washed with 500 ml water for 3 times, 500 ml saturated saline for once, and the organic layer was dried with anhydrous sodium sulfate, concentrated under reduced ide (14.2 g) were added successively, and reacted in room temperature for 8 hours. After the pressure. The solid was pulped with 400 ml ethyl acetate, filtrated and dried to obtain Compound B (35 g), yield: 87.6%.

Step (7.3) Amidation Reaction (Active Ester Method)

Intermediate (8) (40 g) was dissolved in 500 mL methanol, 2N sodium hydroxide solution (17.3 g) was added, stirred at room temperature for 1 hour. The solvent was removed by concentrated under reduced pressure after the reaction was completed, and then dissolved with 2 L dichloromethane and neutralized with 1N hydrochloric acid, and the organic phase was washed once with 500 ml saturated saline. The organic layer was dried with anhydrous sodium sulfate, concentrated under reduced pressure to gain 36 g yellow solid. This intermediate was dissolved in 2 L anhydrous dichloromethane, N, N-dimethylformamide (0.5 ml), diisopropylethylamine (42 ml). EDCI (18.4 g), HOBT (13 g) and N-hydroxy succinimide (13.8 g) were added to react at room temperature for 8 hours. After the reaction was completed, the solvent was dried, dissolved in 2 L dichloromethane, washed with 500 ml water for 3 times, 500 ml saturated sodium bicarbonate solution for once, and 500 ml saturated saline for once, dried with anhydrous sodium sulfate, and dried by distillation, The intermediate was dissolved in 1 L anhydrous dichloromethane, and diisopropyl ethylamine (43 ml) and methylamine hydrochloride (8.1 g) were added, stirred at room temperature for 6 hours. After the reaction was completed, the solvent was removed under reduced pressure and the residual was added to 2 L dichloromethane, washed with 500 ml water for 3 times, and 500 ml saturated saline for once, and the organic layer was dried with anhydrous sodium sulfate, concentrated under reduced pressure. The solid was pulped with 400 ml ethyl acetate, and filtrated and dried to obtain Compound B (34.7 g), yield: 86.9%.

Step (7.4) Amidation Reaction (Direct Condensation Method)

Intermediate (8) (40 g) was dissolved in 1 L methanol, 2N sodium hydroxide solution (17.3 g) was added, stirred at room temperature for 1 hour. When the reaction was completed, the solvent was removed by concentration under reduced pressure, dissolved with 2 L dichloromethane, neutralized with 1N hydrochloric acid, and the organic phase was washed with 500 ml saturated saline for once. The organic layer was dried with anhydrous sodium sulfate, concentrated under reduced pressure to obtain 36 g yellow solid. The intermediate was dissolved in 2 L anhydrous dichloromethane, diisopropylamine (70 ml), EDCI (18.4 g), HOBT (13 g) and methylamine hydrochloride (8.1 g) were added, and stirred under room temperature for 8 hours. the solvent was removed by concentration under reduced pressure after the reaction was completed, the residue was added to 2 L dichloromethane, washed with 500 ml water for 3 times, 500 ml saturated sodium bicarbonate solution for once, and 500 ml saturated saline for once. The organic layer was dried with anhydrous sodium sulfate, concentrated under reduce pressure. The solid was pulped with 400 ml ethyl acetate, and filtrated and dried to obtain Compound B (34.3 g), yield: 85.9%.

Data Characterization of Compound B

1H NMR (400 MHz, Chloroform-d) δ 8.64 (s, 1H), 8.23 (d, J=7.8 Hz, 1H), 8.06 (d, J=8.4 Hz, 1H), 7.98 (d, J=7.8 Hz, 1H), 7.57 (t, J=7.7 Hz, 1H), 7.52 (d, J=8.4 Hz, 1H), 6.57 (s, 1H), 4.93 (s, 1H), 4.62 (d, J=13.7 Hz, 1H), 4.46-4.37 (m, 1H), 4.05-3.98 (m, 2H), 3.96-3.68 (m, 8H), 3.63-3.54 (m, 1H), 3.47-3.35 (m, 1H), 3.07 (d, J=4.8 Hz, 3H), 1.51 (d, J=6.8 Hz, 3H), 1.38 (d, J=6.8 Hz, 3H). LRMS calcd for $C_{25}H_{31}N_6O_3$ ([M+H]$^+$): 463.25, found: 463.36.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for preparing compound of formula III:

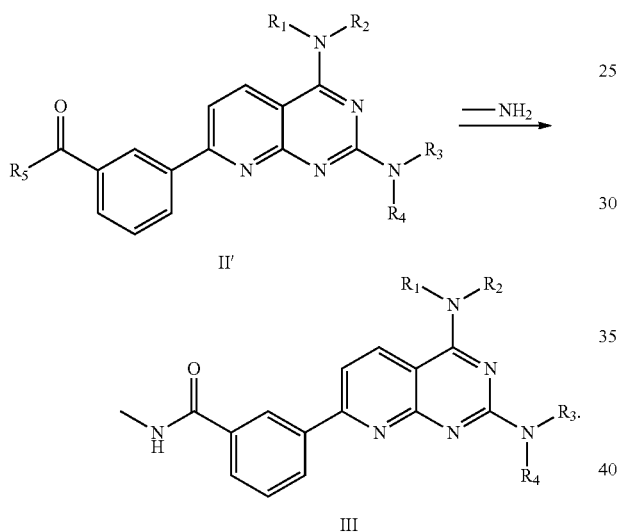

(7) Reacting a compound of formula II' with methylamine or the salt thereof to provide the compound of formula III;

wherein $R_1$, $R_2$, $R_3$ and $R_4$ are each independently selected from the group consisting of substituted or unsubstituted $C_1$-$C_4$ alkyl, substituted or unsubstituted —COO—$C_1$-$C_4$ alkyl, or substituted or unsubstituted —OC(O)—$C_1$-$C_4$ alkyl;

or $R_1$, $R_2$ and the adjacent —N— together form a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

or $R_3$, $R_4$ and the adjacent —N— together constitute a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

$R_5$ is selected from the group consisting of C1-C4 alkoxy, chlorine atom, bromine atom, hydroxyl, or

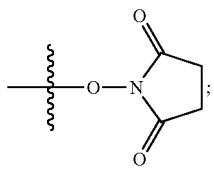 [SMILES: *ON1C(=O)CCC1=O]

the substitution is that one or more hydrogen atoms on a group are replaced by substituents selected from the group consisting of halogens, $C_1$-$C_4$ alkyl;

wherein the methylamine or the salt thereof is selected from the group consisting of methylamine alcohol solution, methylamine aqueous solution, methylamine hydrochloride, or methylamine sulfate.

2. The method of claim 1, wherein, the method further optionally comprises the step:

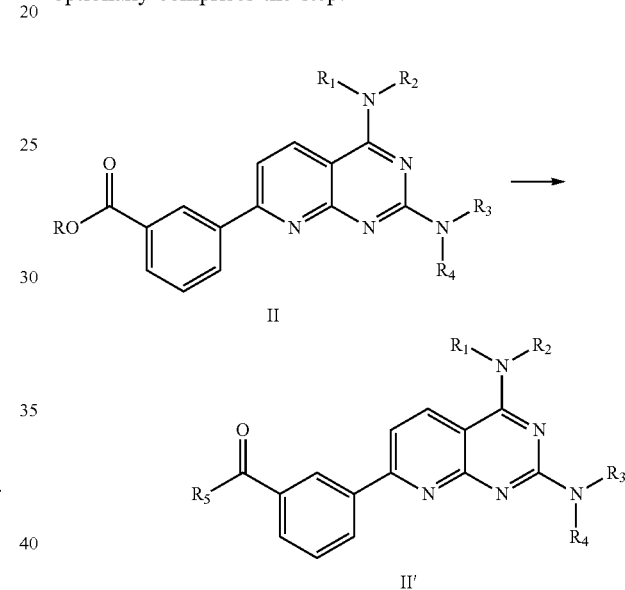

reacting the compound of formula II to provide the compound of formula II';

wherein, R is selected from the group consisting of $C_1$-$C_4$ alkyl; and

RO— and $R_5$— are different groups.

3. The method of claim 2, wherein, in the method, the compound of formula II is prepared by the following step (6):

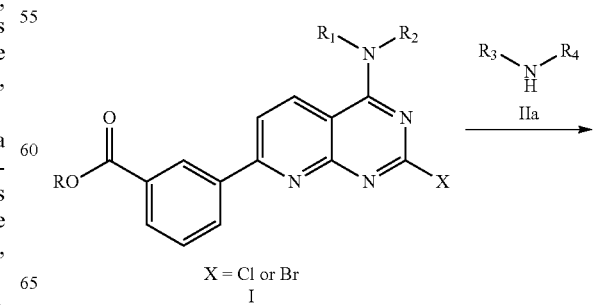

-continued

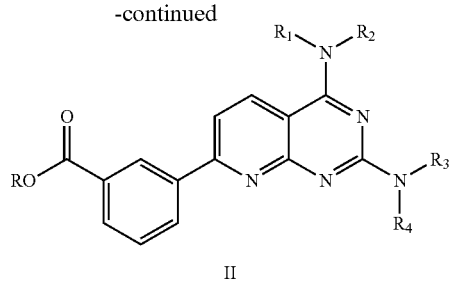

II (6) reacting a compound of formula I with a compound of formula IIa or the salt thereof in an inert solvent to provide the compound of formula II;

wherein:

X is selected from Cl or Br;

$R_1$, $R_2$, $R_3$, and $R_4$ are each independently selected from the group consisting of substituted or unsubstituted $C_1$-$C_4$ alkyl, substituted or unsubstituted $C_1$-$C_4$ ester group;

or $R_1$, $R_2$ and adjacent —N— together form a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

or $R_3$, $R_4$ and adjacent —N— together constitute a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

the substitution is that one or more hydrogen atoms on a group are replaced by substituents selected from the group consisting of alkyl groups of halogens and $C_1$-$C_4$ alkyl.

4. The method of claim 3, wherein, in the method, the compound of formula I is prepared by the following step (5):

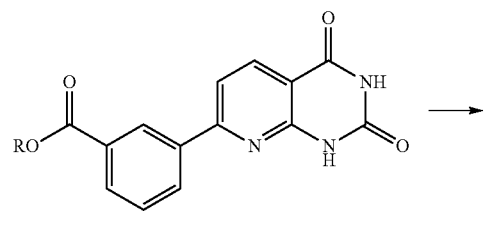

X = Cl or Br
4

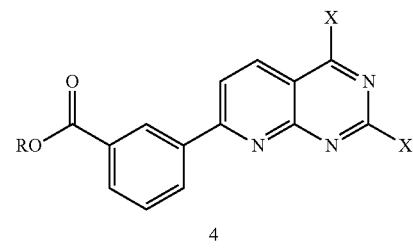

I (5) reacting a compound of formula 4 with a compound of formula Ia or the salt thereof in the inert solvent to provide the compound of formula I;

wherein:

X is selected from Cl or Br;

$R_1$, $R_2$ are each independently selected from the group consisting of substituted or unsubstituted $C_1$-$C_4$ alkyl, substituted or unsubstituted $C_1$-$C_4$ ester group; or $R_1$, $R_2$ and adjacent —N— together form a substituted or unsubstituted 3-10 membered heterocycle, and the heterocycle may contain 1-3 heteroatoms selected from the group consisting of N, O or S; the 3-10 membered heterocycle is monocycle, bicycle, spirocycle or bridged ring;

the substituted means one or more hydrogen atoms on a group are replaced by substituents selected from the group consisting of halogen, and $C_1$-$C_4$ alkyl.

5. The method of claim 4, wherein, in the method, the compound of formula 4 is prepared by the following step (4):

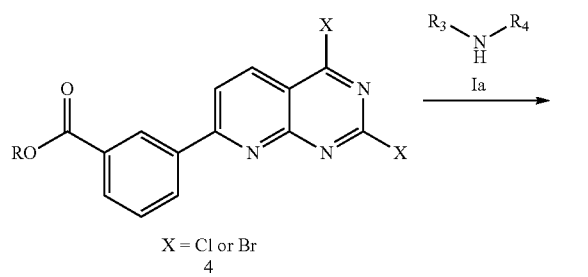

3

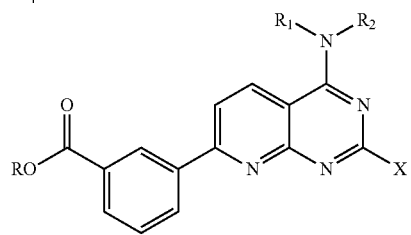

4

X = Cl or Br (4) reacting a compound of formula 3 with halogenated reagent to provide the compound of formula 4, where X is selected from Cl or Br.

6. The method of claim 5, wherein, in the method, the compound of formula 3 is prepared by the step (3):

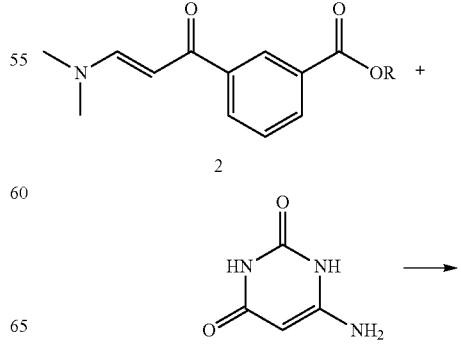

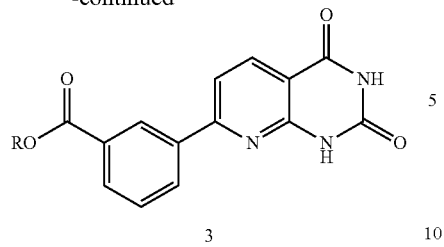

(3) reacting a compound of formula 2 with 6-aminouracil to provide the compound of formula 3.

7. The method of claim 6, wherein in the method, the compound of formula 2 is prepared by the following step (2):

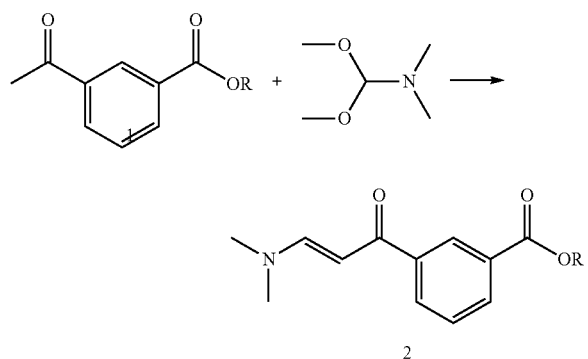

(2) reacting a compound of formula 1 with DMF-DMA in inert solvents to provide the compound of formula 2.

8. A method for preparing a compound of formula A:

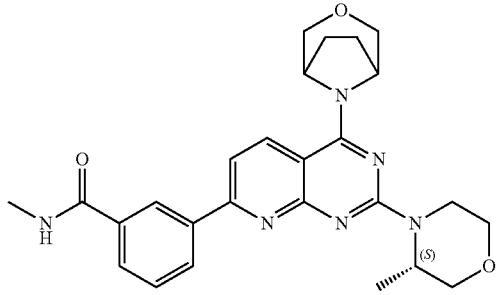

comprising the step:

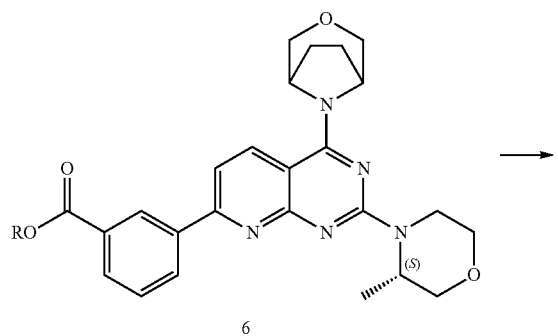

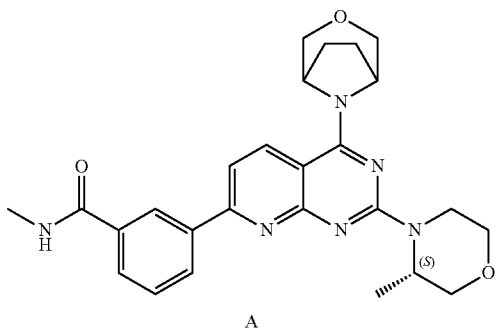

(7a) reacting a compound of formula 6 with methylamine to provide the compound of formula A wherein R is a $C_1$-$C_4$ alkyl.

9. A method for preparing a compound of formula 6, comprising the steps:

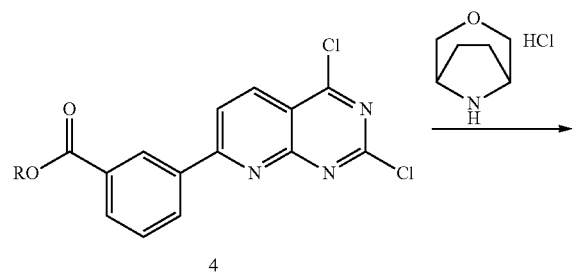

(5a) reacting a compound of formula 4 with 3-oxa-8-azabicyclo[3.2.1]octane hydrochloride in an inert solvent to provide a compound of formula 5;

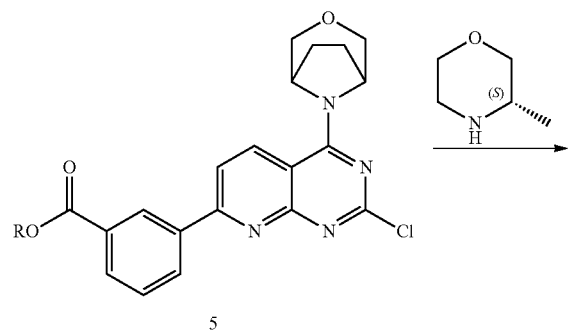

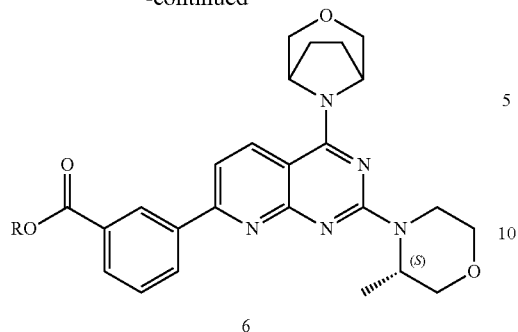

6

(6a) reacting the compound of formula 5 with 3-(S)-3-methylmorpholine in an inert solvent to provide the compound of formula 6, wherein R is C1-C4 alkyl.

10. A method for preparing a compound of formula B

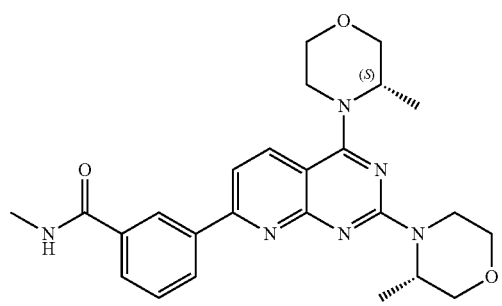

B comprising the step:

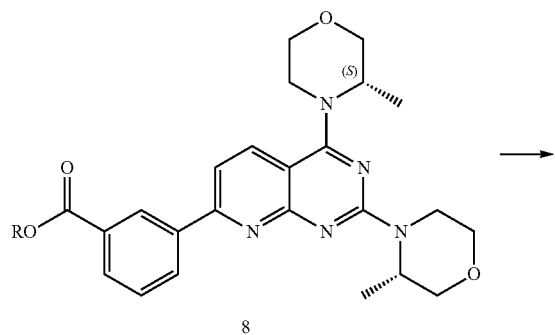

8

→

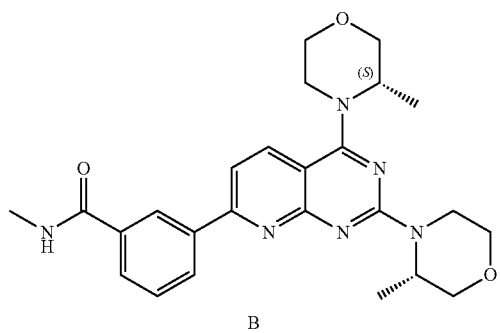

B (7b) reacting a compound of formula 8 with methylamine to provide the compound of formula B, wherein R is $C_1$-$C_4$ alkyl.

11. The method of claim 1, wherein R5 is selected from the group consisting of methoxyl, ethoxy, chlorine atom, bromine atom, hydroxyl, and

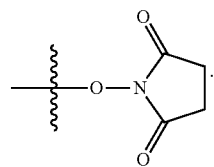 [SMILES: *ON1C(=O)CCC1=O]

.

12. The method of any one of claims 2-10, wherein R is selected from the group consisting of methyl or ethyl.

13. The method of claim 1, wherein the methylamine or the salt thereof is methylamine methanol solution, methylamine ethanol solution.

14. The method of claim 1, wherein the methylamine or the salt thereof is methylamine methanol solution.

* * * * *